(12) United States Patent
Nakaoka et al.

(10) Patent No.: US 6,991,622 B2
(45) Date of Patent: Jan. 31, 2006

(54) DISPOSABLE SHORTS

(75) Inventors: Kenji Nakaoka, Sadamitsu-cho (JP); Masaru Fujioka, Sadamitsu-cho (JP); Satoshi Maeda, Sadamitsu-cho (JP); Kazuyo Mori, Sadamitsu-cho (JP)

(73) Assignee: Livedo Corporation, Ehime (JP)

( * ) Notice: Subject to any disclaimer, the term of this patent is extended or adjusted under 35 U.S.C. 154(b) by 382 days.

(21) Appl. No.: 10/182,156

(22) PCT Filed: Feb. 8, 2001

(86) PCT No.: PCT/JP01/00875

§ 371 (c)(1),
(2), (4) Date: Jul. 25, 2002

(87) PCT Pub. No.: WO01/58401

PCT Pub. Date: Aug. 16, 2001

(65) Prior Publication Data

US 2003/0023219 A1 Jan. 30, 2003

(30) Foreign Application Priority Data

Feb. 8, 2000 (JP) ..................................... 2000-030982

(51) Int. Cl.
*A61F 13/15* (2006.01)

(52) U.S. Cl. ............................. 604/385.201; 604/385.3
(58) Field of Classification Search ............... 604/385.3, 604/385, 201, 385.23, 385.22, 378
See application file for complete search history.

(56) References Cited

U.S. PATENT DOCUMENTS

| 5,624,424 A | 4/1997 | Saisaka et al. |
| 5,817,087 A | * 10/1998 | Takabayashi et al. .. 604/385.29 |
| 6,149,638 A | * 11/2000 | Vogt et al. ............. 604/385.01 |
| 6,306,122 B1 | * 10/2001 | Narawa et al. .......... 604/385.3 |

FOREIGN PATENT DOCUMENTS

| EP | 1 027 874 | 8/2000 |
| GB | 2 268 389 | 1/1994 |

* cited by examiner

*Primary Examiner*—Larry I. Schwartz
*Assistant Examiner*—C. Lynne Anderson
(74) *Attorney, Agent, or Firm*—Jordan and Hamburg LLP

(57) ABSTRACT

Inventive disposable underpants are provided with an underpants member formed of a first sheet as an outermost layer and a second sheet located inside the first sheet; an absorbent member provided on the second sheet at the inner side of the underpants member; and a trunk fittable elastic member for fitting the trunk tightly held between the first and second sheets, wherein absorbent member fixing sheets each folded to form an upper and a lower portions are transversely arranged below the absorbent member, and the upper portions of the absorbent member fixing sheets are joined with a lower surface of the absorbent member, whereas the lower portions thereof are joined with an upper surface of the second sheet. Thus, even if the disposable underpants were formed using a thin absorbent member, the absorbent member could suppress a lateral leak of urine without being twisted while the disposable underpants were worn.

5 Claims, 7 Drawing Sheets

DISPOSABLE SHORTS

TECHNICAL FIELD

The present invention relates to disposable underpants highly fittable to a crotch portion of a wearer without being twisted even if a very thin absorbent member is used.

BACKGROUND ART

Elastic members for fitting the trunk of a wearer are known to be provided in addition to elastic members for the legs and those for the waist in order to fit disposable underpants or a disposable diaper to a wearer (for example, Japanese Unexamined Patent Publication No. 4-166150).

The disposable underpants and the like as above have an effect of a comfortable wearing feeling due to high fittability since a clearance is unlikely to be created between the wearer and the absorbent member particularly by elastic forces of the elastic members for fitting the trunk.

However, in the case of using a highly flexible thin absorbent member such as an absorbent member of a low Metsuke having a relatively small amount of pulp fibers or an absorbent member in the form of a thin sheet not using pulp fibers, there have been cases where widthwise shrinking forces by the elastic members for fitting the trunk and longitudinal shrinking forces by the elastic members for the legs act on the absorbent member to thereby twist the absorbent member. Metsuke is weight of fiber per unit area. If the absorbent member is twisted, a clearance is likely to be created between the wearer and the absorbent member. Such a clearance makes it difficult to prevent a lateral leak of urine and the like and reduces a fittability, whereby a comfortable wearing feeling cannot be obtained.

In view of the problems residing in the prior art, an object of the present invention is to provide disposable underpants which can prevent a lateral leak of urine and the like, has a high fittability and provides a comfort wearing feeling even if a highly flexible thin absorbent member is used.

DISCLOSURE OF THE INVENTION

The present invention is directed to disposable underpants, comprising an underpants member formed of a first sheet as an outermost layer and a second sheet located inside the first sheet; an absorbent member provided on the inner side of the underpants member; and an elastic member for the waist, elastic members for the leg, a trunk fittable elastic member which are tightly held between the first and second sheets, wherein absorbent member fixing sheets each folded to form an upper and a lower portions are transversely arranged below the absorbent member, and the upper portions of the absorbent member fixing sheets are joined with a lower surface of the absorbent member, whereas the lower portions thereof are joined with a upper surface of the second sheet.

With the above construction, elastic forces (shrinking forces) of the respective elastic members tightly held between the first and second sheets do not act on the absorbent member due to the flexure of the absorbent member fixing sheets. Thus, the absorbent member is not twisted. Further, since the absorbent member is joined with the second sheet via the vertically folded absorbent member fixing sheets, displacements of the absorbent member can be suppressed.

BEST MODE FOR CARRYING OUT THE INVENTION

Hereinafter, embodiments of the present invention are described in detail with reference to the accompanying drawings.

Figure 1:
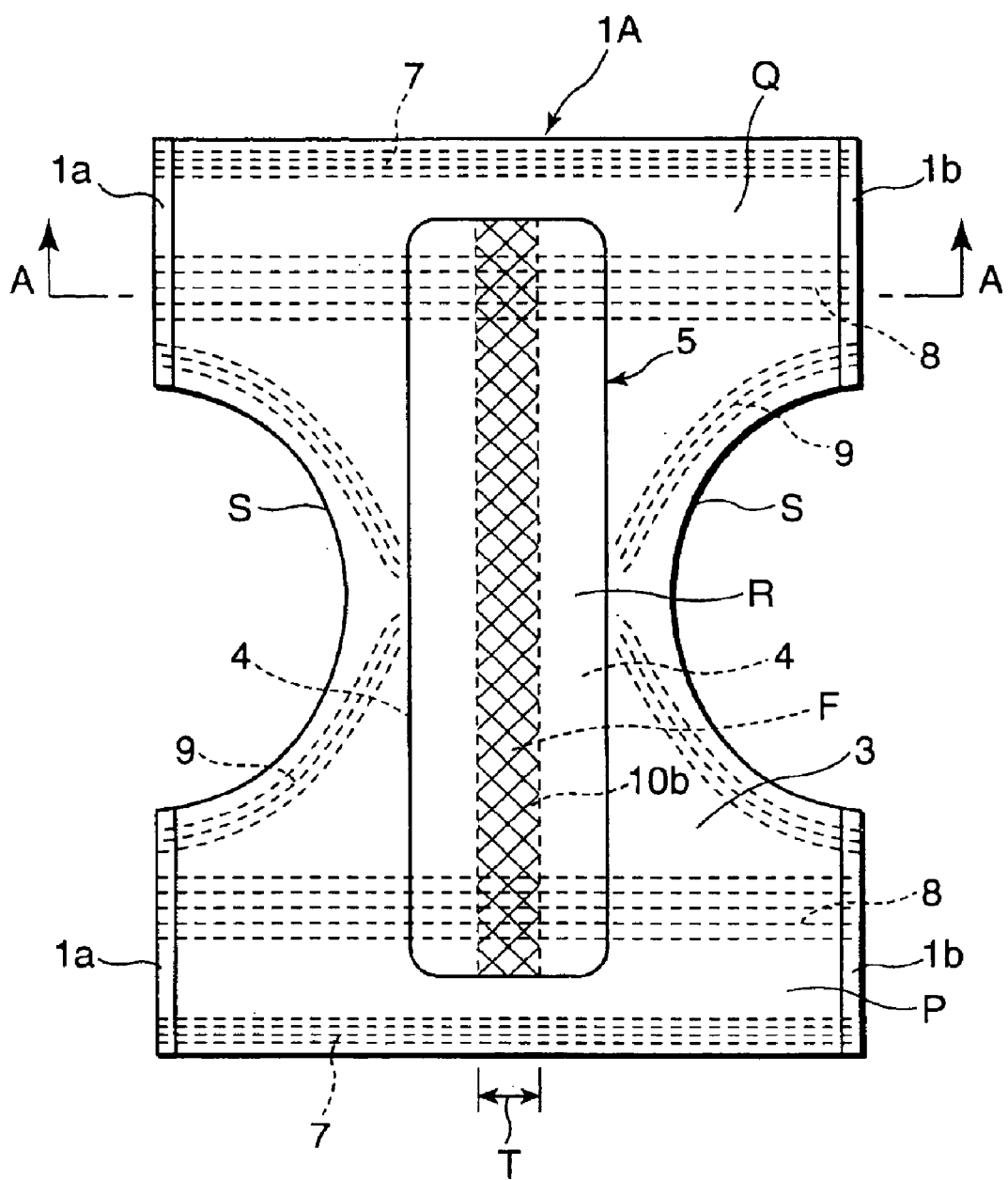
FIG. 1 is a front view showing a developed state of disposable underpants according to a first embodiment.
Figure 2:
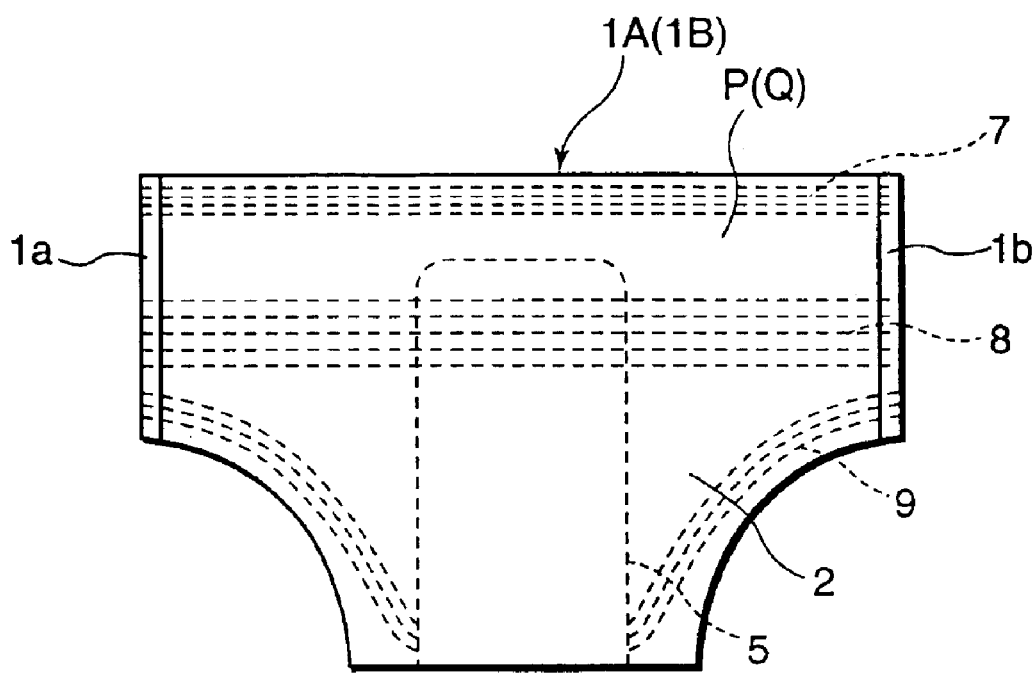
FIG. 2 is a front view showing a used state of the disposable underpants.
Figure 3A:
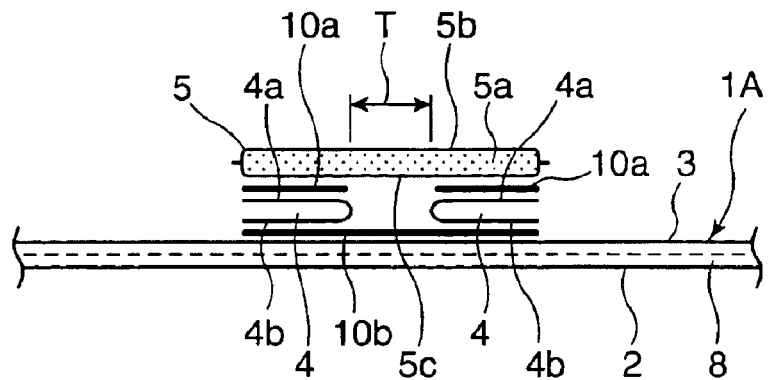
FIGS. 3A, 3B and 3C are schematic sections corresponding to a section along A—A of FIG. 1.
Figure 3B:
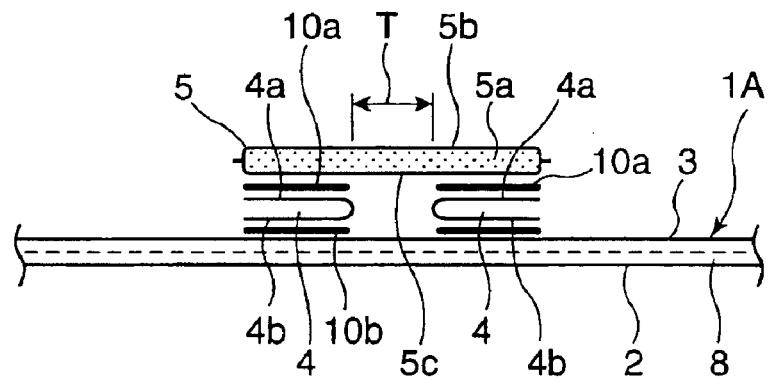
Figure 3C:
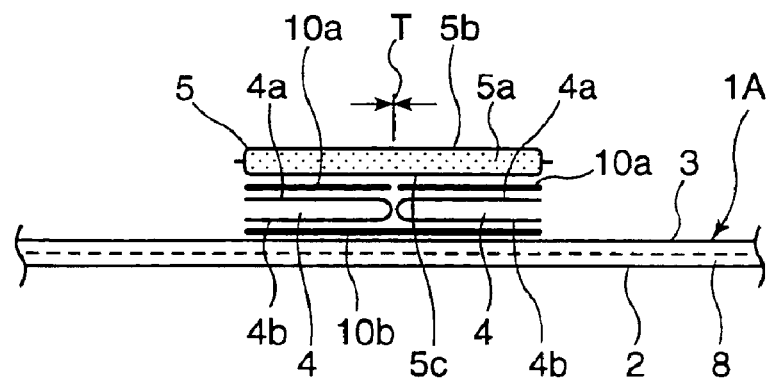
Figure 4:
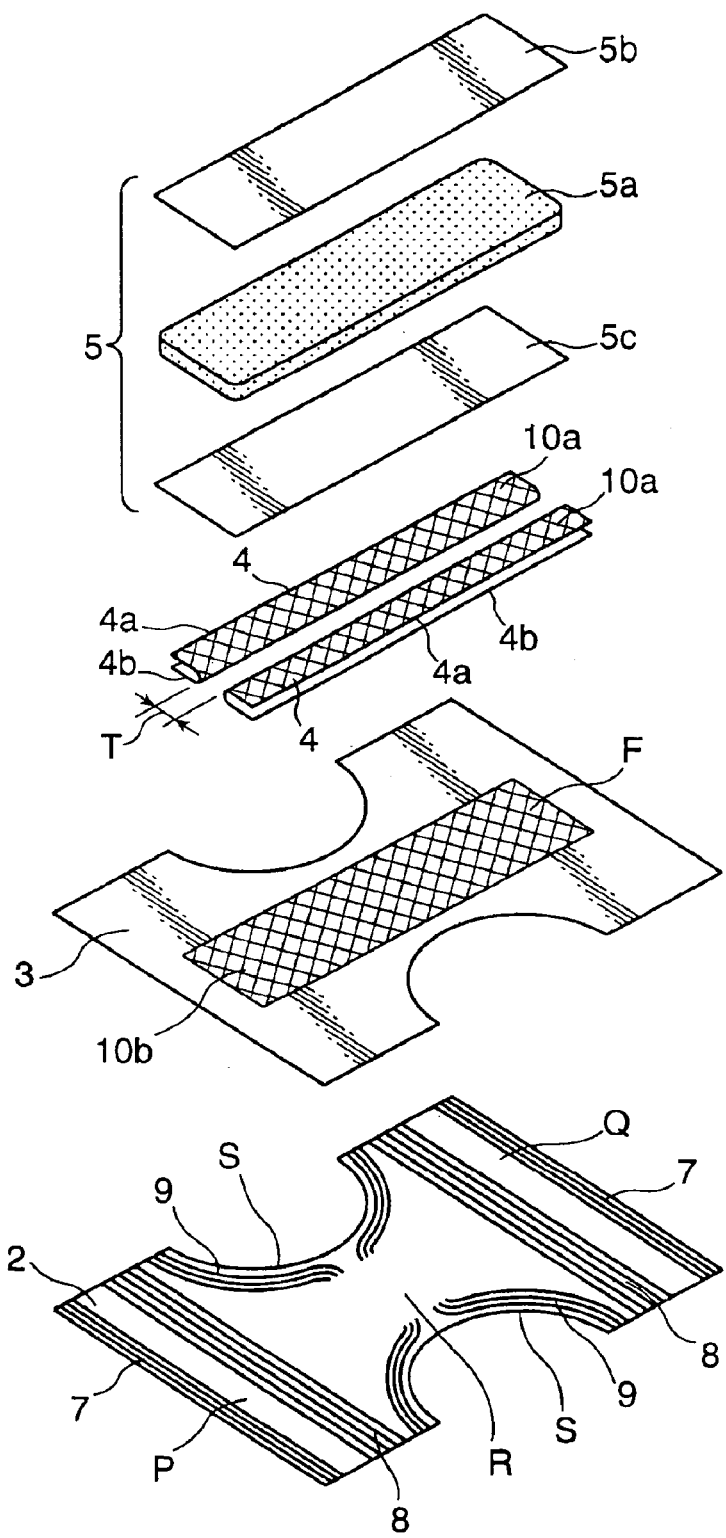
FIG. 4 is an exploded perspective view of the disposable underpants.

FIGS. 1 to 4 show disposable underpants 1A according to a first embodiment, wherein FIG. 1 is a front view showing a developed state of the disposable underpants 1A, FIG. 2 is a front view showing a used state of the disposable underpants 1A, FIGS. 3A, 3B and 3C are schematic sections corresponding to a section along A—A of FIG. 1, and FIG. 4 is an exploded perspective view of the disposable underpants 1A.

The disposable underpants 1A in the developed state of FIG. 1 are folded along forward and backward directions, i.e. opposite side portions 1a, 1b of a front part P and a back part Q of the disposable underpants 1A are placed one over the other and joined, thereby being assembled into the used state of FIG. 2. As shown in FIG. 4, the disposable underpants 1A are basically comprised of a first sheet 2 which is an outermost sheet, a second sheet 3 provided inside the first sheet 2, a pair of left and right absorbent member fixing sheets 4 which are mounted on the inner side of the underpants main body, and an absorbent member 5. The first sheet 2 and the second sheet 3 form an underpants main body The first sheet 2 is an element forming the main body of the disposable underpants 1A, thus forming an outer shape of the underpants 1A. Leg openings S are formed at the opposite sides of a crotch portion R between the front part P and the back part P of the first sheet 2. The first sheet 2 is preferably made of a nonwoven fabric. Nonwoven fabrics (may partly contain hydrophilic fibers such as rayon) made of polyethylene, polypropylene, polyester or composite fibers of these are preferable in order to prevent a steamy feeling and to be agreeable to the touch. Further, a water-repellent treatment may be applied to the fibers themselves or the nonwoven fabric itself. Instead of the nonwoven fabric, various kinds of plastic films having a liquid impermeability, but a gas permeability may be used or laminates of theses plastic films and the nonwoven fabrics may be used.

A plurality of elastic members 7 for the waist and a plurality of trunk fittable elastic member 8 (elastic member 8 for fitting the trunk) are extendably and shrinkably provided along the widthwise direction of the underpants on the upper surfaces of the front and back parts P, Q of the first sheet 2, and a plurality of elastic members 9 for the leg are extendably and shrinkably provided along the peripheral edge of each leg opening S. Strips or strings of a natural rubber, a synthetic rubber such as polyurethane or a thermoplastic elastomer film may be used as the elastic members 7 to 9. In the case that the first and second sheets 2, 3 are made of an extendable and shrinkable nonwoven fabric, the elastic members 8 for fitting the trunk may be omitted.

The elastic members 9 for the leg are normally so provided as to cross the crotch portion R for the continuous production. The elastic members 9 for the leg may be adhered to the crotch portion R. However, by not adhering the elastic members 9 to the crotch portion R and then cutting only the elastic members 9 at the crotch portion R by a cutter, the shrinking forces of the elastic members 9 can be prevented from acting on the crotch portion R (see FIG. 4).

The second sheet 3 has substantially the same shape as the first sheet 2 and is an element forming the main body of the disposable underpants 1A together with the first sheet 2, thus forming the outer shape of the underpants. Similar to the first sheet 2, the second sheet 3 is also preferably made of a nonwoven fabric. Nonwoven fabrics (may partly contain hydrophilic fibers such as rayon) made of polyethylene, polypropylene, polyester or composite fibers of these are preferable. Liquid permeable plastic films or gas permeable, but liquid impermeable plastic films may be used as the second sheet 3, but it is preferable to use nonwoven fabrics for both the first sheet 2 and the second sheet 3 in order to prevent a steamy feeling.

The elastic members 7 for the waist, the elastic members 8 for fitting the trunk and the elastic members 9 for the leg are adhered to the first and second sheets 2, 3 by, for example, a hotmelt adhesive while being held between these sheets 2, 3. Instead of being adhered to the second sheet 3, the elastic members 7 for the waist may be held in folded portions 2b formed by folding elongated front and rear ends of the first sheet 2 and adhered as shown in FIG. 7C.

The absorbent member 5 is constructed such that a core 5a containing a high water-absorbent polymer powder is held and sealed between a top sheet 5b on the upper surface of the core 5a and a back sheet 5c on the bottom surface of the core 5a. The core 5a essentially contains the high water-absorbent polymer powder. Pulp fibers, heat-fusible fibers, nonwoven fabrics, or tissues may be additionally mixed or laminated. Since the present invention is particularly suitable for the disposable underpants using a highly flexible thin absorbent member, an absorbent member in which a high water-absorbent polymer powder is merely adhered to a nonwoven fabric without using pulb fibers at all or an absorbent member in which a high water-absorbent composite composition obtained by composing and unifying microfibrils (having a diameter of 2 $\mu$m or smaller) obtained from cellulose or the like and a high water-absorbent polymer powder is laminated on a nonwoven fabric (Japanese Unexamined Patent Publication No. 10-168230, etc.) may be used as the absorbent member 5. The absorbent member 5 may take a sandglass shape or an other shape. The top sheet 5b is preferably made of a hydrophilic nonwoven fabric obtained by applying a hydrophilic treatment to a nonwoven fabric (may partly contain hydrophilic fibers such as rayon) made of polyethylene, polypropylene, polyester or composite fibers of these if necessary. A liquid impermeable plastic film or a fine porous film having a gas permeability each made of a polyethylene and the like, or a nonwoven fabric to which a water-repellent treatment was applied may be used as the back sheet 5c.

The absorbent member 5 is adhered to the upper surface of the second sheet 3 via the pair of left and right absorbent member fixing sheets 4 as shown in FIGS. 3A to 3C. Although the fixing sheets 4 are not particularly limited, they are preferably made of a polyolefin plastic film or a nonwoven fabric having a relatively high Metsuke of 30 g/m$^2$ or more. Although not specifically shown, standing strips (cuffs) for preventing a lateral leak of urine and the like may be provided at the opposite sides of the upper surface of the absorbent member 5.

The pair of left and right absorbent member fixing sheets 4 have substantially the same length as the absorbent member 5 and are each folded to form an upper portion 4a and a lower portion 4b. In other words, the fixing sheets 4 are arranged between the second sheet 3 and the absorbent member 5 while being vertically folded. In FIG. 3A, the fixing sheets 4 are provided at the left and right sides below the absorbent member 5 while being spaced apart by a clearance T extending in longitudinal direction.

The upper portions 4a of the fixing sheets 4 are joined with the lower surface of the absorbent member 5 via joining portions 10a, whereas the lower portions 4b thereof are joined with the upper surface of the second sheet 3 via a joining portion 10b. Preferably, a hotmelt adhesive is used to form the joining portions 10a, 10b. Instead of applying the hotmelt adhesive to the entire surfaces (entire surface in longitudinal direction) of the joining portions 10a, 10b, it is preferable to intermittently apply the hotmelt adhesive to the surfaces of the joining portions 10a, 10b. For example, a method for applying the hotmelt adhesive in lines along the longitudinal or widthwise direction of the joining portions 10a, 10b, a method for applying the hotmelt adhesive in dots, a method for applying the hotmelt adhesive while continuously drawing spiral traces, a method for forming a network aggregate from fine fibers of the hotmelt adhesive and the like may be counted.

The hotmelt adhesive may be applied to the lower surface of the absorbent member 5 or to the upper portions 4a of the fixing sheets 4 to form the joining portions 10a. In either case, the hotmelt adhesive is so applied not to protrude out from the upper portions 4a of the fixing sheets 4.

The hotmelt adhesive may be applied to the lower portions 4b of the fixing sheets 4 in order to form the joining portion 10b. However, in order to apply the hotmelt adhesive to the upper surface of the second sheet 3 located at the clearance T between the left and right lower portions 4b, the hotmelt adhesive is preferably applied to the upper surface of the second sheet 3 as shown as a hatched portion F in FIG. 4. In either case, the hotmelt adhesive is so applied not to protrude out from the lower portions 4b of the fixing sheets 4.

When the absorbent member 5 thus joined with the second sheet 3 via the left and right fixing sheets 4 is pressed, only the lower surface of the absorbent member 5 located at the clearance T is directly joined with the second sheet 3 by the joining portion 10b. Although a center portion of the absorbent member 5 is shown not to be joined with the second sheet 3 in FIG. 3A in order to clarify the positional relationship of the respective elements, it is actually joined over the width of the clearance T.

In the thus formed disposable underpants 1A, the absorbent member 5 is joined with the second sheet 3 only over the width of the clearance T between the fixing sheets 4, and the elastic forces of the respective elastic members 7 to 9 are taken up by the flexure of the fixing sheets 4. Thus, the elastic forces of the elastic members 7 to 9 are unlikely to act on the absorbent member 5, which is therefore unlikely to be twisted. Further, since the absorbent member 5 is directly joined with the second sheet, it is free from displacements.

However, the narrower the clearance T, the more the elastic forces of the respective elastic members 7 to 9 are unlikely to act on the absorbent member 5. Thus, a construction having no clearance T at all as shown in FIG. 3C is preferable.

On the other hand, as shown in FIG. 3B, the lower surface of the absorbent member 5 located at the clearance T may not be joined with the second sheet 3. Specifically, the hotmelt adhesive is applied to left and right sides of the upper surface of the second sheet 3 to form joining portions 10b having the same width as the fixing sheets 4 without being applied to the portion of the upper surface of the second sheet 3 located at the clearance T.

With this construction, the absorbent member 5 is not directly joined with the second sheet 3, and the elastic forces of the respective elastic members 7 to 9 are absorbed by the flexure of the fixing sheets 4. Thus, the elastic forces of the respective elastic members 7 to 9 hardly act on the absorbent member 5 to prevent the absorbent member 5 from being twisted.

In any of the above constructions, since the opposite widthwise sides of the absorbent member 5 are joined with the second sheet 3 via the vertically folded fixing sheets 4, the displacements of the absorbent member 5 both along longitudinal direction and along widthwise direction can be suppressed and the opposite sides of the absorbent member 5 are prevented from being twisted.

In this way, the absorbent member 5 is not twisted even if the highly flexible thin absorbent member 5 is used. Thus, no clearance is created between a wearer and the absorbent member 5 and a lateral leak of urine and the like can be prevented. Further, since the elastic forces of the respective elastic members 7 to 9 between the first and second sheets 2, 3 are not hindered by the absorbent member 5, fittability can be improved and a comfortable wearing feeling can be obtained.

Figure 5:
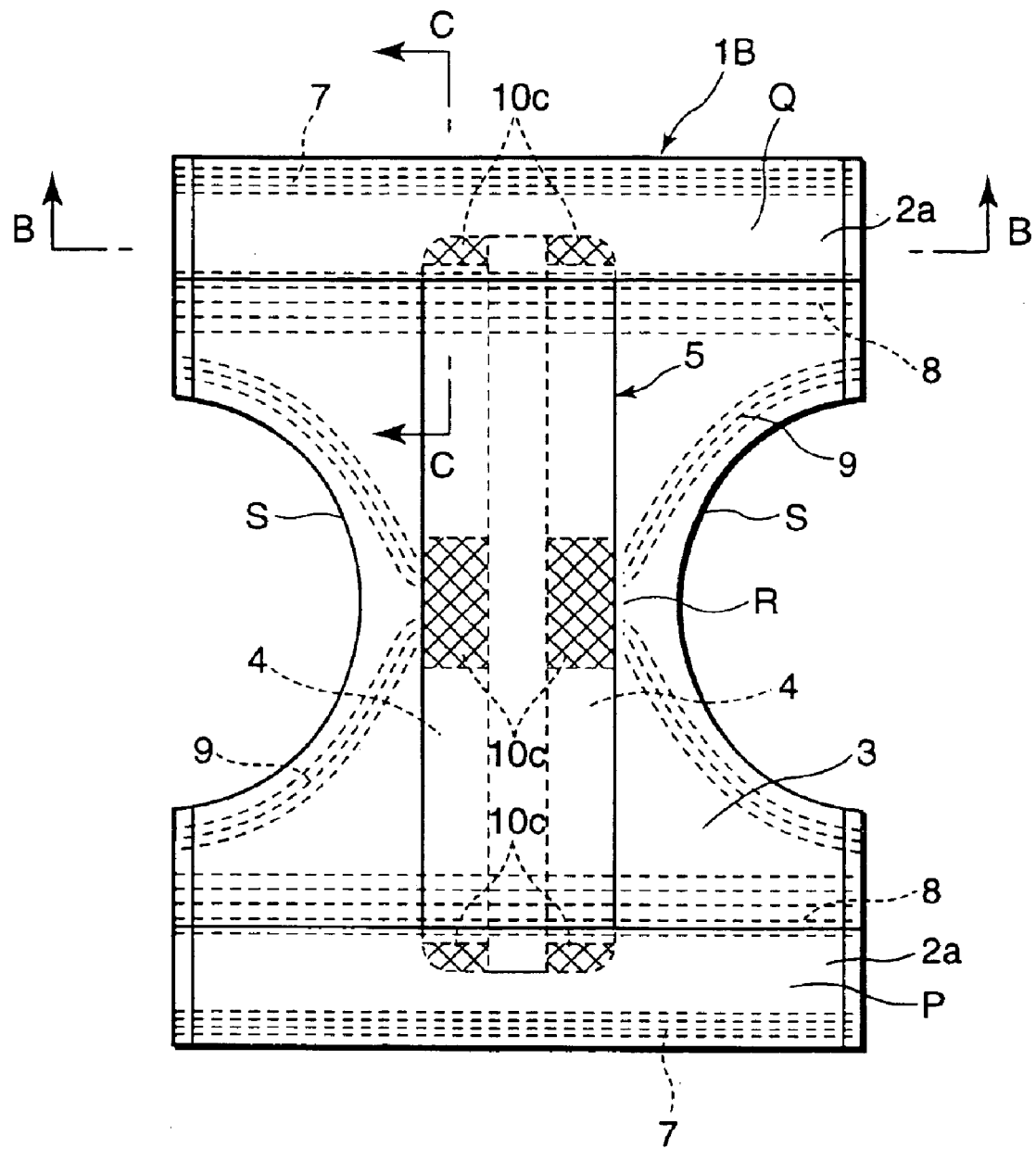
FIG. 5 is a front view showing a developed state of disposable underpants according to a second embodiment.
Figure 6:
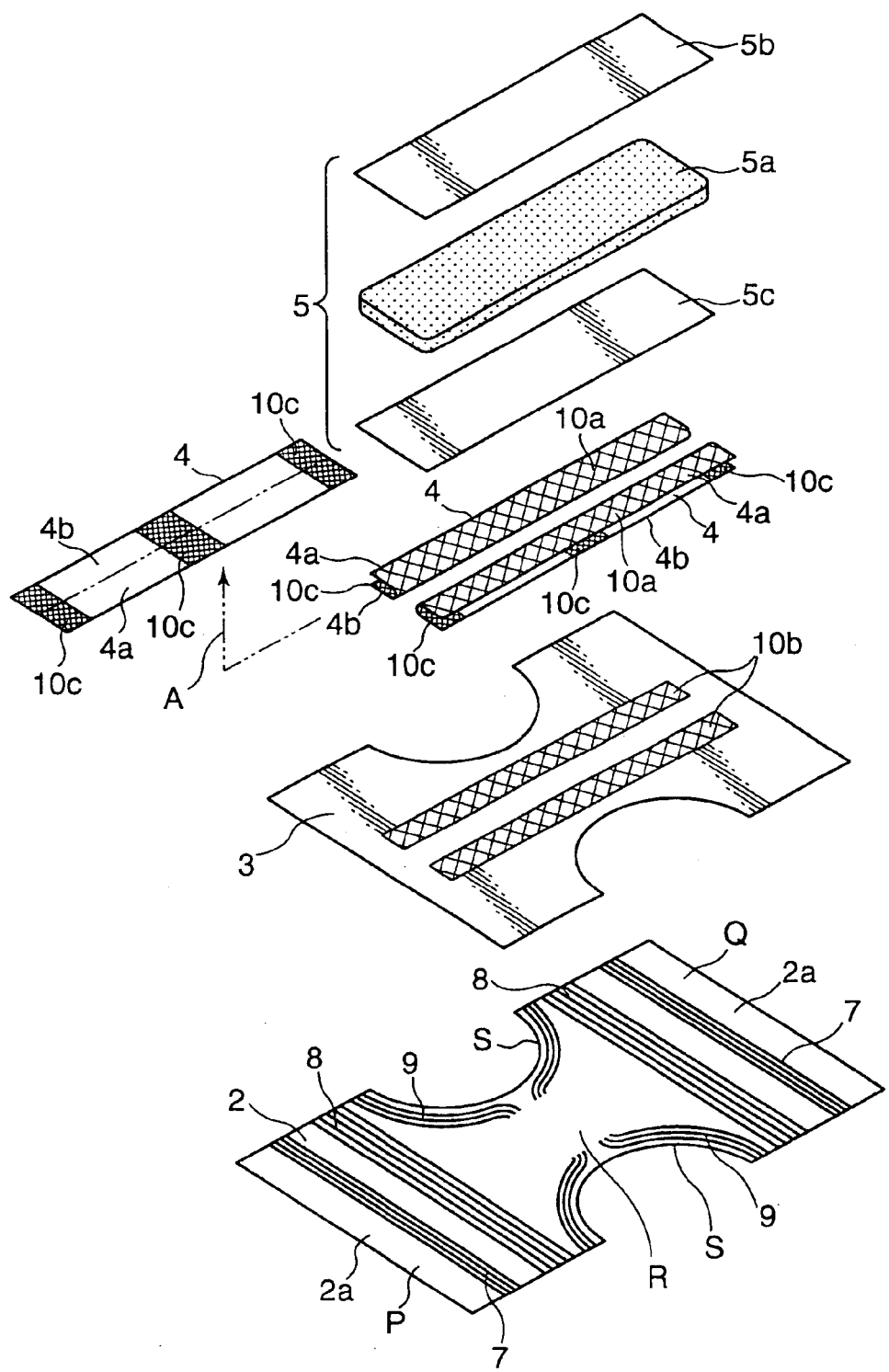
FIG. 6 is an exploded perspective view of the disposable underpants.
Figure 7A:
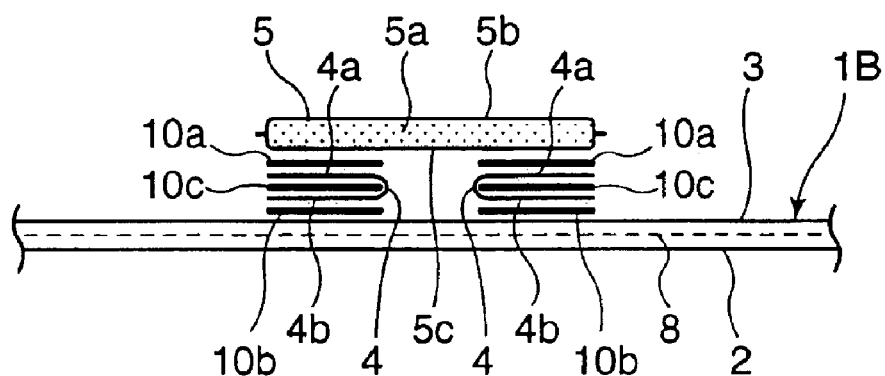
FIGS. 7A, 7B and 7C are a schematic section along B—B of FIG. 5, a schematic section along C—C of FIG. 5 and a schematic section of a modification corresponding to the section along C—C of FIG. 5.
Figure 7B:
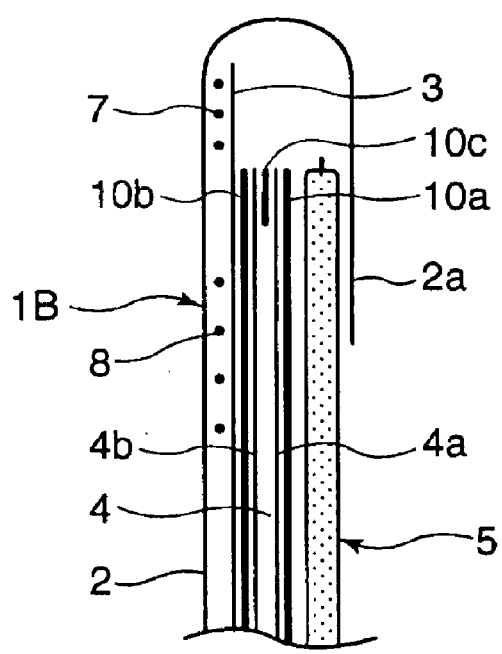
Figure 7C:
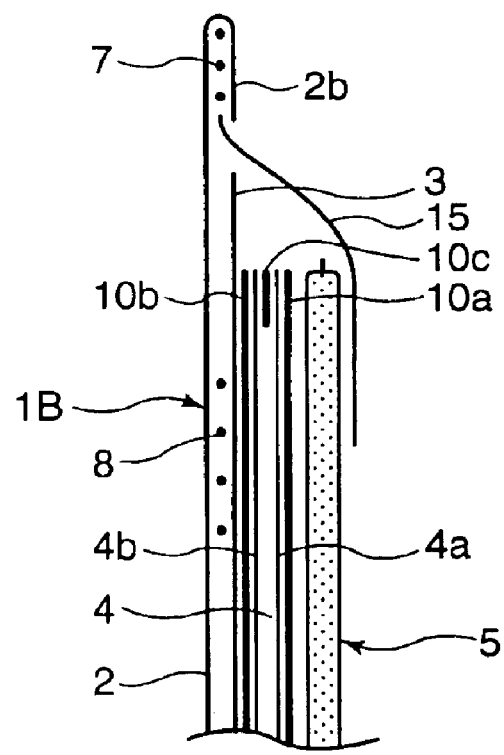

FIGS. 5 to 7 show disposable underpants 1B according to a second embodiment, wherein FIG. 5 is a front view showing a developed state of the disposable underpants 1B, FIG. 6 is an exploded perspective view of the disposable underpants 1B, FIG. 7A is a schematic section corresponding to a section along B—B of FIG. 5, and FIGS. 7B and 7C are schematic sections corresponding to a section along C—C of FIG. 5.

The disposable underpants 1B of the second embodiment are formed such that absorbent member fixing sheets 4 are provided at left and right positions between a second sheet 3 and an absorbent member 5 while being spaced apart by a clearance T, upper portions 4a are joined with the lower surface of the absorbent member 5 via joining portions 10a, lower portions 4b are joined with the upper surface of the second sheet 3 via joining portions 10b, and the upper and lower portions 4a, 4b of the fixing sheets 4 are partly joined with each other at their intermediate, front and rear portions in longitudinal directions by joining portions 10c. The narrower the clearance T, the more preferable. As in the modification shown in FIG. 3C, the clearance T may be zero.

The disposable underpants 1B of the second embodiment differ from the disposable underpants 1A of the first embodiment in that the front and rear ends of the first sheet 2 are extended from the second sheet 3 by the length of folded portions 2a. The front and rear folded portions 2a may be so short as to be sufficient to cover an area where elastic members 7 for the waist are provided, and make the appearance of an waist end portion better. As shown in FIGS. 5 and 7D, the front and rear folded portions 2a may be so long as to be sufficient to cover the front and rear ends of the absorbent member 5 with respect to longitudinal direction. In this construction, the front and rear ends of the absorbent member 5 can be prevented from being turned up and from being displaced in forward and backward directions by joining the ends of the folded portions 2a of the first sheet 2 with the upper surface of the front and rear ends of the absorbent member 5 with respect to longitudinal direction. A construction in which folded portions 2b are formed to be short and ends of separate sheets 15 toward the absorbent member 5 are joined with the upper surface of the absorbent member 5 as shown in FIG. 7C has also the same effects. The ends of the separate sheets 15 toward the folded portions 2b may be joined by being held between the first sheet 2 and the folded portions 2b. A hydrophilic or water-repellent nonwoven fabric can be preferably used as the separate sheets.

The construction of the disposable underpants 1B also differs from that of the disposable underpants 1A in that the upper portions 4a and the lower portions 4b of the fixing sheets 4 are partly joined on the inner sides thereof. Specifically, as shown in a developed state of the fixing sheet 4 indicated by an arrow A of two-dot-chain line in FIG. 6, the inner sides of the upper portion 4a and the lower portion 4b of the fixing sheet 4 are joined at the intermediate, front and rear portions along longitudinal direction by the respective joining portions 10c. Welding means by heat or ultrasonic waves, and an adhering means by a hotmelt adhesive may be adopted to form the joining portions 10c. In the case of forming the joining portions 10c by applying the hotmelt adhesive, the hotmelt adhesive is applied to the inner sides of the lower portions 4b or to the inner sides of the upper portions 4a of the fixing sheets 4.

In the disposable underpants 1B thus formed, since the absorbent member 5 is securely joined with and fixed to the second sheet 3 forming the outer shape of the underpants by the joining portions 10c, the lower portions 4b of the fixing sheets 4 and the joining portions 10b, the absorbent member 5 is not bent in forward and backward directions while the disposable underpants 1B are worn. Further, displacements of the absorbent member 5 along forward and backward directions can also be prevented. Since the joining portions 10c joining the upper and lower portions 4a, 4b of the fixing sheets 4 are partly provided at the front, rear and intermediate portions, the influence of the elastic forces of the respective elastic members on the absorbent member 5 is small and, therefore, the absorbent member 5 is hardly twisted. As described above, in the case of, for example, adopting the construction in which the front and rear ends of the absorbent member 5 are pressed by the folded portions 2a of the first sheet 2 or the separate sheets 15, the joining portions 10c joining the upper and lower portions 4a, 4b of the fixing sheets 4 may be provided only at the intermediate portions.

In the case that the upper and lower portions 4a, 4b of the fixing sheets 4 are partly joined, the joining portions 10b joining the fixing sheets 4 and the second sheet 3 are preferably transversely spaced apart as in the modification of FIG. 3B lest the lower surface of the absorbent member 5 should be joined with the second sheet 3 (FIG. 6). This is because it is not necessary to directly join the absorbent member 5 with the second sheet 3 since the absorbent member 5 is indirectly firmly joined with the second sheet 3 by joining the upper and lower portions 4a, 4b of the fixing sheets 4. This also makes it difficult for the elastic forces of the respective elastic members 7 to 9 to act on the absorbent member 5, with the result that the absorbent member 5 becomes more difficult to twist.

As is clear from the above description, in the construction according to claim 1 of the present invention, the absorbent member fixing sheets are arranged at the left and right positions between the second sheet and the absorbent member, the upper portions thereof are joined with the lower surface of the absorbent member, whereas the lower portions thereof are joined with the upper surface of the second sheet which is a side of the underpants main body facing the wearer's skin. Thus, the elastic forces of the respective elastic members do not act on the absorbent member by being taken up by the flexure of the absorbent member fixing sheets and, therefore, the absorbent member is not twisted. Further, since the absorbent member is firmly joined with the second sheet via the absorbent member fixing sheets, the absorbent member is free from displacements.

Accordingly, even if a highly flexible thin absorbent member is used, a space is unlikely to be created between the wearer and the absorbent member. Thus, a lateral leak of urine and the like can be prevented and a comfortable wearing feeling can be obtained due to a higher fittability.

In the construction according to claim 2, since the elastic forces of the respective elastic members become more unlikely to act on the absorbent member by providing the clearance extending in longitudinal direction, the twisting of the absorbent member can be further suppressed.

In the construction according to claim 3, since the upper and lower portions of the absorbent member fixing sheets are partly joined with each other, the absorbent member is firmly joined with the second sheet via the absorbent member fixing sheets. Thus, the displacements of the absorbent member can be suppressed.

In the construction according to claim 4, the appearance of the waist end of the underpants becomes very beautiful by forming the folded portions by folding the front and rear ends of the first sheet on the second sheet.

In each of the construction according to claim 5 in which the end portions of the folded portions formed by folding the front and rear ends of the first sheet on the second sheet and the construction according to claim 6 in which the separate sheets are joined with the upper surfaces of the front and rear portions of the absorbent member, the displacements of the absorbent member can be suppressed.

What is claimed is:

1. Disposable underpants, comprising:

an underpants member formed of a first sheet as an outermost layer and a second sheet located inside the first sheet;

an absorbent member provided on the second sheet at the inner side of the underpants member;

a trunk fittable elastic member tightly held between the first and second sheets;

absorbent member fixing sheets each being folded to form an upper and a lower portion, said absorbent member fixing sheets being transversely arranged below the absorbent member, the upper portions of the absorbent member fixing sheets being joined with a lower surface of the absorbent member, and the lower portion of each of the absorbent member fixing sheets being joined with an upper surface of the second sheet;

a front folded portion and a rear folded portion formed by folding the first sheet at front and rear ends of the underpants with respect to the longitudinal direction on the second sheet, the respective end portions of the front and rear folded portions being joined with the upper surfaces of front and rear end portions of the absorbent member with respect to the longitudinal direction.

2. Disposable underpants according to claim 1, wherein the absorbent member fixing sheets are spaced apart while defining a clearance extending in a longitudinal direction of the underpants.

3. Disposable underpants according to claim 1, wherein the upper and lower portions of the absorbent member fixing sheets are partly joined with each other.

4. Disposable underpants according to claim 1, further comprising a front separate sheet for covering a portion between an edge of the front folded portion and a front edge of the absorbent member and a rear separate sheet for covering a portion between an edge of the rear folded portion and a rear edge of the absorbent member, wherein an end of said each separate sheet toward the folded portion is tightly held between the first sheet and the folded portion, whereas an end thereof toward the absorbent member is joined with the upper surface of the absorbent member.

5. Disposable underpants according to claim 1, wherein the absorbent member includes a highly flexible thin absorbent member.

* * * * *